United States Patent
Lanting et al.

(10) Patent No.: US 6,309,553 B1
(45) Date of Patent: Oct. 30, 2001

(54) PHASE SEPARATOR HAVING MULTIPLE SEPARATION UNITS, UPFLOW REACTOR APPARATUS, AND METHODS FOR PHASE SEPARATION

(75) Inventors: Jelte Lanting, Washington Township; John L. Murphy, III, Voorhees, both of NJ (US)

(73) Assignee: Biothane Corporation, Camden, NJ (US)

( * ) Notice: Subject to any disclaimer, the term of this patent is extended or adjusted under 35 U.S.C. 154(b) by 0 days.

(21) Appl. No.: 09/406,976

(22) Filed: Sep. 28, 1999

(51) Int. Cl.[7] ............................... C02F 1/00; B01D 43/00
(52) U.S. Cl. ........................ 210/802; 210/521; 210/522
(58) Field of Search .................................. 210/522, 521, 210/802

(56) References Cited

U.S. PATENT DOCUMENTS

| | | |
|---|---|---|
| Re. 32,597 | 2/1988 | Pette . |
| 4,089,782 | 5/1978 | Huebner . |
| 4,122,017 | 10/1978 | Tanabe et al. . |
| 4,156,644 | 5/1979 | Richard . |
| 4,165,285 | 8/1979 | Wind et al. . |
| 4,446,018 | 5/1984 | Cerwick . |
| 4,477,344 | 10/1984 | Olszewski et al. . |
| 4,609,460 | 9/1986 | Vellinga . |
| 4,618,418 | 10/1986 | Heijnen et al. . |
| 4,622,147 | 11/1986 | Vellinga . |
| 4,664,802 | 5/1987 | Lee . |
| 4,758,339 | 7/1988 | Vellinga . |
| 4,780,206 | 10/1988 | Beard et al. . |
| 5,116,505 | 5/1992 | Lourens et al. . |
| 5,230,794 | 7/1993 | Heijnen et al. . |
| 5,338,447 | 8/1994 | Vellinga . |
| 5,500,118 | 3/1996 | Coenen et al. . |
| 5,565,098 | 10/1996 | Vellinga . |
| 5,855,785 | 1/1999 | Heijnen et al. . |
| 5,904,850 | 5/1999 | Vellinga . |

FOREIGN PATENT DOCUMENTS 0 808 805 A1   11/1997   (EP) .

Primary Examiner—Chester T. Barry
(74) Attorney, Agent, or Firm—Akin, Gump, Strauss, Hauer & Feld, L.L.P.

(57) ABSTRACT

A phase separator, upflow reactor apparatuses and methods for separating phases are provided. The phase separator includes a first separation unit and a second separation unit, each of which has walls defining a coagulation area. One of the walls adjoins a deflector inclined to the horizontal and vertical. The separator also includes a plurality of parallel plates spaced from each other and vertically and horizontally inclined which each have a lower edge. The other wall of the separator adjoins one of the parallel plates and the deflector extends below and across the lower edges of the parallel plates. Each of the first and the second separation units is capable of separating a gas from a liquid by diverting the gas around one wall of each of the separation units and by creating a circulation of the liquid around at least one of the parallel plates such that liquid is directed into the coagulation area. The upflow reactor apparatus includes phase separators having multiple units alone or in combination with a further separator in series arrangements. The methods include providing an upflow of gas and liquid within an upflow reactor apparatus having phase separators as noted herein, providing a liquid circulation around at least one of the parallel plates of the separator by diverting gas flow to one or more gas collecting areas such that the liquid circulation provides a downwardly directed flow around the parallel plates and liquid is directed to one or more coagulation areas. Gas from the gas collecting area or areas is directed from the upflow reactor apparatus through a gas outlet.

46 Claims, 6 Drawing Sheets

PHASE SEPARATOR HAVING MULTIPLE SEPARATION UNITS, UPFLOW REACTOR APPARATUS, AND METHODS FOR PHASE SEPARATION

BACKGROUND OF THE INVENTION

Various designs of phase separation devices and settling devices are known for the separation and/or purification of liquids. Such devices are useful in many fields including water treatment, physico-chemical wastewater treatment, biological wastewater treatment, food processing, the production of pharmaceuticals and other biotechnological applications. Such reactors can include fermentation type systems in which a biomass solid is introduced to a fluidized bed system along with waste water, and fermentation is allowed to proceed. In such systems, gas can be generated and needs to be removed from the system.

One such useful phase separation apparatus is disclosed in U.S. Pat. No. 5,855,785 of Heijnen et al. The three-phase separator in that reference uses parallel plates in combination with a deflector plate to create gas-lift circulation which not only contributes to separation of the solid, liquid and gas phases, but operates to maintain biomass in the reactor longer to enhance fermentation in the lower portion of a fluidized bed apparatus having the three-phase separator at the top of the apparatus. While such device is highly effective in retaining granular biomass, it is not optimized for the clarification of suspended solids from the separator effluent. Further, while more than one such three-phase separator may be installed in a reactor, due to the space required for such units, such multiple use is limited. Further, such separators have independent and generally conically shaped settling zones, such that use of more than one such separator does not further optimize or enhance clarification of suspended solids from the separator effluent U.S. Pat. No. 5,904,850 of Vellinga describes a settling device for fluids having solid particles, liquid and gas which has V-shaped, angled caps which are placed in the settling device on top of a large, transversely extending and inverted, single V-shaped cap which is asserted to trap some of the gas under the "V." The remaining solid, liquid and gas are passed under the obliquely angled V-shaped caps to direct gas under a further cap to an area where the gas can pass out through the top. Particulates which did not settle by gravity under the V-shaped caps are subjected to a spray head.

Reissue Pat. No. 32,597 of Pette describes an apparatus for anaerobic purification of waste water which includes an anaerobic purification area which has four after-settling compartments. Each of such compartments includes an interruption in the wall of the settling compartment for allowing water and particulate to enter the settling compartment and an opening at the bottom for allowing sludge that settles out to be directed downwardly into the reaction zone. The apparatus also has gas collection areas which may be connected to gas collection casings. Clarified liquid is removed by weirs between the compartments.

Other separation devices include those which are placed in a turbulent flow of waste water which use the undercurrent of the turbulent liquid to draw solids from quiet zones within the separation area. The quiet zones or clarification areas are formed by placing a vertically extending wall within the flow of waste water to reduce turbulence downstream of the wall and direct solid back to the lower portion of the flowing liquid. Gas is removed by bubbling up through the quiet zones. Such devices are described, for example, in U.S. Pat. Nos. 4,780,206 and 4,446,018.

While the above described devices and similar devices are useful for separation, difficulties are sometimes encountered, particularly in fluidized bed reactors, in minimizing upflow velocity to ensure a high level of separation and in providing optimal clarification of suspended solids from separated effluent As a result, there is a need in the art to improve existing phase separators, and particularly three-phase separators, to provide a device which is useful for separating phases and which can work with a fluidized bed or other upflow reactor apparatus, for example for fermentation, waste water treatment or other process to effectively remove solids or maintain solids within a reaction zone of the fluidized bed apparatus without interrupting the flow of clarified liquid. For difficult to separate media, there is a need in the art to improve separation efficiency, and, for more easily separable media, there is a need in the art to further improve such separators to allow for an overall reduction in reactor size in order to thereby reduce cost and expenses associated with the operation of larger upflow reactor apparatuses having phase separators.

Further, there is a need for a fluidized bed apparatus which has a more optimal differential flow velocity to increase the amount of solids, such as biomass, separated or retained within a reaction zone and to allow for more effective and more efficient gas and liquid separation.

SUMMARY OF THE INVENTION

The invention includes a phase separator capable of being used with an upflow reactor apparatus and comprising a first separation unit and a second separation unit, each of the first and the second separation units comprises (a) a first wall having a first side and a second side and a second wall having a first side and a second side, the second side of the first wall and the first side of the second wall defining a coagulation area, wherein the first wall adjoins a deflector inclined to the horizontal and vertical; and (b) a plurality of parallel plates spaced from each other and vertically and horizontally inclined, each of the parallel plates having a lower edge, wherein the second wall adjoins one of the parallel plates and the deflector extends below and across the lower edges of the parallel plates, wherein each of the first and the second separation units is capable of separating a gas from a liquid by diverting the gas to the second side of the second wall of each separation unit and by creating a circulation of the liquid around at least one of the parallel plates such that liquid is directed into the coagulation area.

In one embodiment of the phase separator, the phase separator comprises a plurality of separation units, each separation unit having (a) a first wall having a first side and a second side and a second wall having a first side and a second side, the second side of the first wall and the first side of the second wall defining a coagulation area, wherein the first wall adjoins a deflector inclined to the horizontal and vertical; and (b) a plurality of parallel plates spaced from each other and vertically and horizontally, inclined and each of the parallel plates having a lower edge, wherein the second wall adjoins one of the parallel plates and the deflector extends below and across the lower edges of the parallel plates, wherein each of separation units is capable of separating a gas from a liquid by diverting the gas to the second side of the second wall of each separation unit and by creating a circulation of the liquid around at least one of the parallel plates such that liquid is directed into the coagulation area In addition to the phase separator, the invention includes an upflow reactor apparatus, comprising a phase separator, wherein the phase separator comprises a first separation unit and a second separation unit secured within the upflow reactor apparatus, each of the first and the second separation units comprising (a) a first wall having a first side and a second side and a second wall having a first side and a second side, the second side of the first wall and the first side of the second wall defining a coagulation area, wherein the first wall adjoins a deflector inclined to the horizontal and vertical; and (b) a plurality of parallel plates spaced from each other and vertically and horizontally inclined, each of the parallel plates having a lower edge, wherein the second wall adjoins one of the parallel plates and the deflector extends below and across the lower edges of the parallel plates, wherein each of the first and the second separation units is capable of separating a gas from a liquid by diverting the gas to the second side of the second wall of each separation unit and by creating a circulation of the liquid around at least one of the parallel plates such that liquid is directed into the coagulation area.

An upflow reactor apparatus is also within the invention which comprises a first phase separator and a second separator which may be the same or different from the first phase separator, wherein the at least one second separator is located on top of and longitudinally spaced from the first phase separator within the upflow reactor apparatus, wherein at least one of the first phase separator or the second separator comprises a first separation unit and a second separation unit secured within the upflow reactor apparatus, each of the first and the second separation units comprising: (a) a first wall having a first side and a second side and a second wall having a first side and a second side, the second side of the first wall and the first side of the second wall defining a coagulation area, the first wall adjoining a deflector inclined to the horizontal and vertical; and (b) a plurality of parallel plates spaced from each other and vertically and horizontally inclined, each of the parallel plates having a lower edge, the second wall adjoining one of the parallel plates and the deflector extending below and across the lower edges of the parallel plates.

The invention further includes a method of separating a liquid and a gas within an upflow reactor apparatus having a reaction zone, comprising (a) providing an upflow of liquid and gas within the upflow reactor apparatus such that the liquid and gas flow upwardly from the reaction zone into a phase separator having a first separation unit and a second separation unit, wherein each of the first and the second separation units have (i) a first wall having a first side and a second side and a second wall having a first side and a second side, the second side of the first wall and the first side of the second wall defining a coagulation area, the first wall adjoining a deflector inclined to the horizontal and vertical and (ii) a plurality of parallel plates spaced from each other and vertically and horizontally inclined, each of the parallel plates having a lower edge, the second wall adjoining one of the parallel plates and the deflector extending below and across the lower edges of the parallel plates; (b) providing a liquid circulation around at least one of the parallel plates by diverting gas flow to a gas collecting area between the second side of the second wall of the first separation unit circulation provides a downwardly directed flow around the parallel plates of each of the first and the second separation units and liquid is directed toward the coagulation area; and (c) directing the diverted gas from the gas collecting area out of the upflow reactor apparatus through a gas outlet.

In a further embodiment of the invention, the invention includes a method of separating a liquid and a gas within an upflow reactor apparatus having a reaction zone, comprising (a) providing an upflow of the liquid and the gas within the upflow reactor apparatus such that the liquid and gas flow upwardly from the reaction zone into a first phase separator having a first wall having a first side and a second side and a second wall having a first side and a second side, the second side of the first wall and the first side of the second wall defining a coagulation area, the first wall adjoining a deflector inclined to the horizontal and vertical, and a plurality of parallel plates spaced from each other and vertically and horizontally inclined, each of the parallel plates having a lower edge, the second wall adjoining one of the parallel plates and the deflector extending below and across the lower edges of the parallel plates; (b) providing a liquid circulation around the parallel plates by diverting gas away from the coagulation area to a gas collecting area, wherein the liquid circulation provides a downwardly directed flow around the parallel plates of the first phase separator and liquid is directed toward the coagulation area; (c) directing the diverted gas from the gas collecting area out of the upflow reactor apparatus through a gas outlet; (d) directing liquid from the coagulation area into a second separator which may be the same or different from the first phase separator and which is located above the first phase separator; and (e) removing liquid from the upflow reactor apparatus through an outlet above the at least one second separator.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, like numerals are used to indicate like elements throughout. In the drawings.

DETAILED DESCRIPTION OF THE INVENTION

Figure 1:
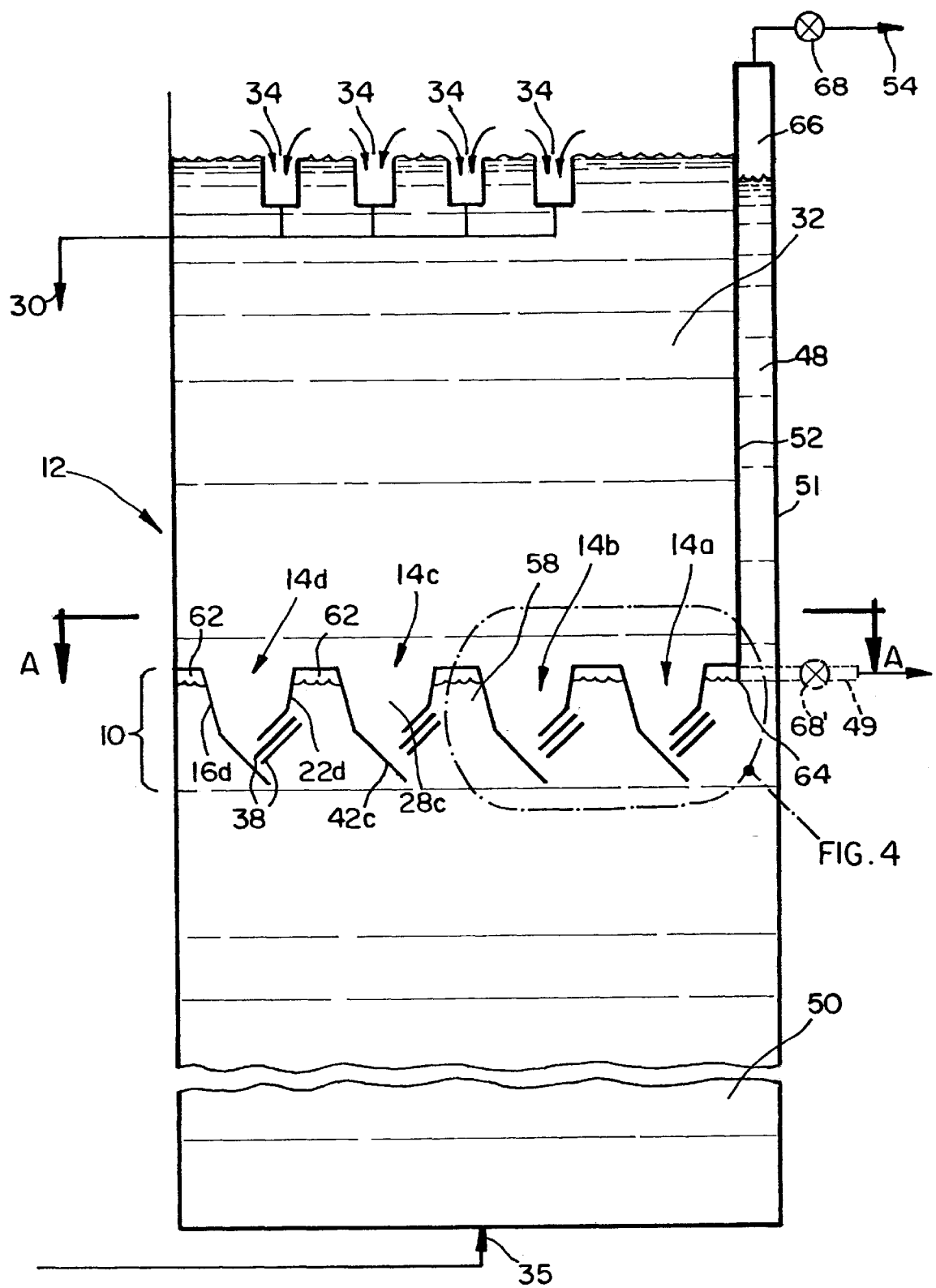
FIG. 1 is a cross sectional schematic representation of an upflow reactor apparatus and phase separator according to the invention.

The invention includes a phase separator and upflow reactor apparatuses which have a phase separator according to the invention and which have combinations of such phase separators. In addition, the invention includes methods for separating liquids and gases, and preferably solids. The phase separators and upflow reactor apparatuses of the invention include the unique feature of enhancing solids retention and improving flow characteristics of upflow reactor apparatuses by using multiple separation units and/or by using such units alone or in series. The unique features of the design of the present invention allow for variation and optimization of separation space within an upflow reactor apparatus, providing significantly enhanced separation efficiency. Further, the multiple separation units in the phase separator according to the invention enable the formation of a single, large clarification zone which may extend to the fully available transverse width of the apparatus having the phase separator, and which, due to the enhanced solids retention and improved flow characteristics, is highly efficient in clarification and has a maximized clarification zone. The available clarification zone is maximized due to the design of the phase separators as well as the creation of a gas-liquid interface between separation units in the phase separator which is below the clarification area, thereby avoiding turbulence caused by upflowing gas in the quiescent, clarification zone as well as avoiding the need for additional space in the clarification zone for displacement and removal of gas.

The phase separators of the invention further provide for a coagulation area in each separation unit which allows for turbulent mixing of upwardly and downwardly flowing solids thereby enhancing the return rate of larger coagulated particles to the reaction zone. Upwardly flowing smaller particles, which are not otherwise caught by coagulating solids or in currents around the parallel plates in the separation units described below and directed downwardly, pass into the clarification area or quiescent zone and are allowed to settle and fall downwardly back to the reaction zone. As such, the phase separators and upflow reactor apparatuses of the invention not only provide enhanced flow characteristics, but also provide for significantly improved levels of solids retention.

The following is a detailed description of preferred embodiments of the invention and should not be considered to be limiting. The multiple separation units are described in detail herein as well as upflow reactor apparatuses which include such multiple separation units.

One important feature of the use of multiple separation units in accordance with the invention as described herein which creates a significant improvement over prior art separators is the creation of a gas-liquid interface resulting from the use of multiple units which forms in the areas between the separation units. Such gas-liquid interface below the clarification zone differs from prior designs which separate the gaseous phase primarily at the top of the apparatus, and allows for a maximum use of available clarification space as well as provides for a less turbulent clarification zone. Other important features of the invention will be described in detail below.

Certain terminology is used in the following description for convenience only and is not limiting. The words "lower" and "upper," "top" and "bottom," and "upward" and "downward" designate directions in the drawings to which reference is made. The terminology includes the words above specifically mentioned, derivatives thereof and words of similar import.

Figure 3:
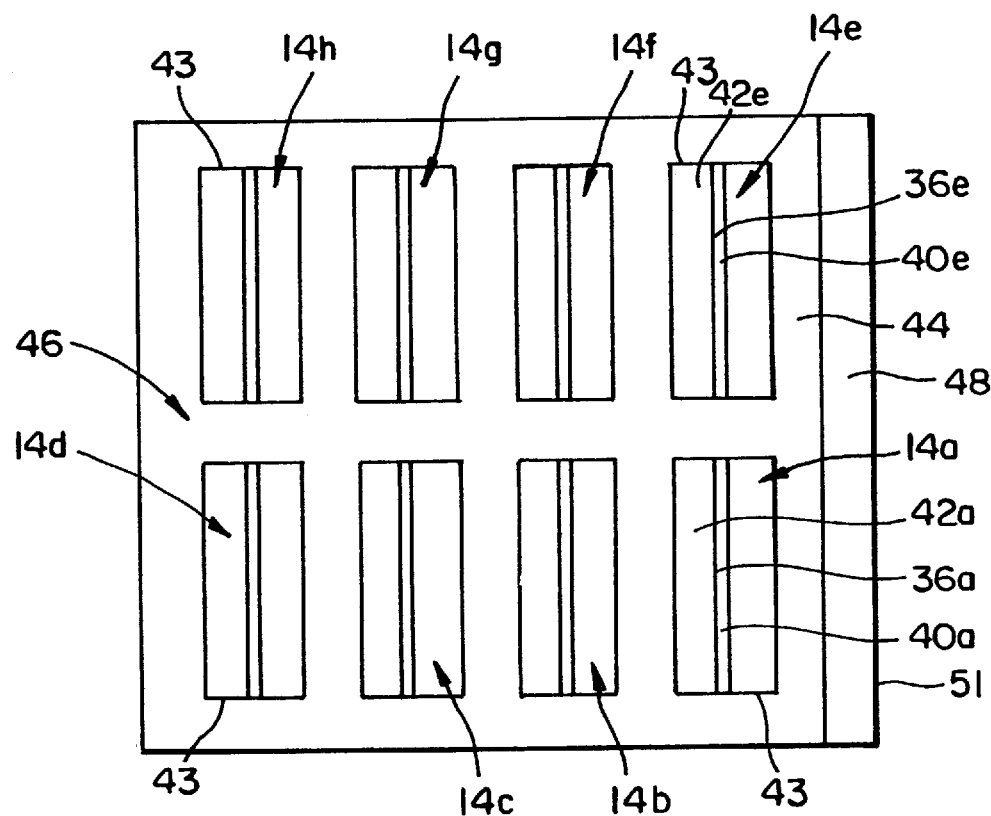
FIG. 3 is a cross sectional schematic representation of the upflow reactor apparatus of FIG. 1 taken along line A—A.
Figure 4:
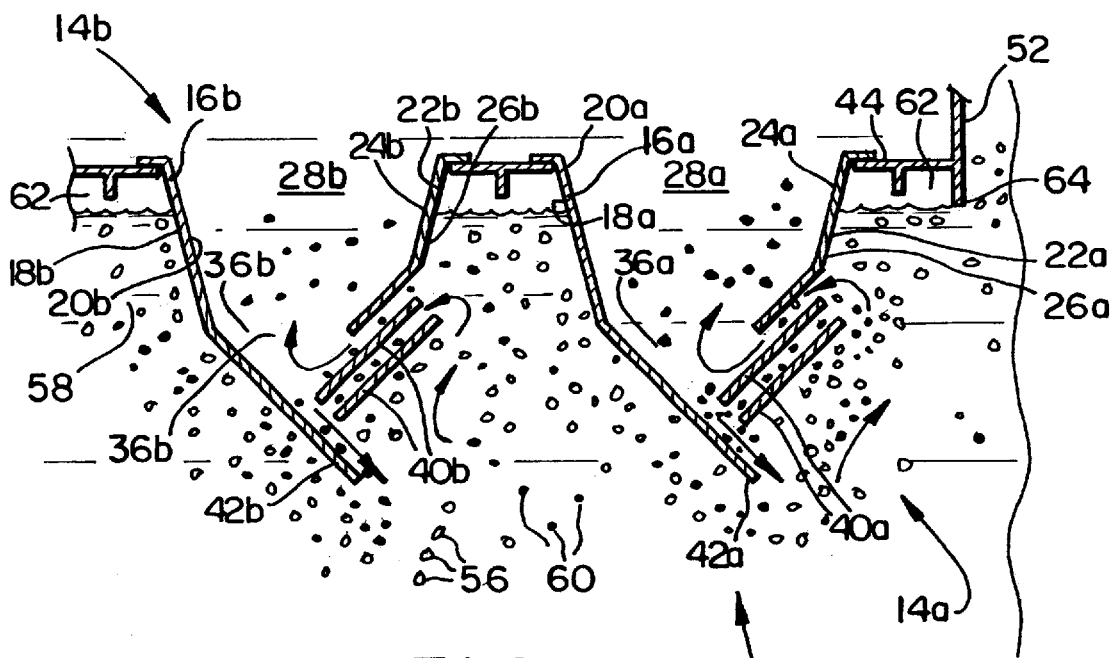
FIG. 4 is an enlarged cross sectional schematic representation of two phase separation units within the phase separator of FIG. 1.

Referring now to the drawings in detail, there are shown in FIGS. 1, 3, 4 and 7 a phase separator generally designated as 10 and an upflow reactor apparatus generally designated as 12 in accordance with one preferred embodiment of the present invention. The phase separator 10 has at least two phase separation units 14, including a first separation unit 14$a$ unit and a second separation unit 14$b$, and preferably, as shown in FIG. 1 it also has a plurality of such separation units including separation units 14$c$ and 14$d$. FIG. 3, which shows the phase separator 10 and upflow reactor apparatus 12 in cross section along line A—A also shows units 14$e$, 14$f$, 14$g$ and 14$h$. Since, in FIGS. 1, 3, 4 and 7, each of the units 14 is similar, all uses of a general reference number, such as 14, when used herein, would mean any or all of the like separation units 14$a$–14$f$, unless otherwise specified. Each separation unit 14 includes a first wall 16 having a first side 18 and a second side 20 and a second wall 22 having a first side 24 and a second side 26. The second side 20 of the first wall 16 and the first side 24 of the second wall 22 define a coagulation area 28 as shown in FIGS. 1 and 4. While the separation units as shown include flat walls 16, 22 such that the coagulation areas of the separation units would have a preferred and generally rectangular cross section as shown in FIG. 3, it should be understood based on this disclosure that the first wall 16 and the second wall 22 can be adapted to be curved and meet to form an overall generally circular, oblong, oval or other desired cross sectional configuration without departing from the spirit of invention.

In the coagulation area 28, solids may be moving upwardly into the clarification zone as described below and downwardly after settling out of clarified liquid in the clarification zone. As such, the area 28 affords an opportunity for solids to coagulate which creates a sufficiently high setting velocity. Such two directional flow within the coagulation area 28 creates a fairly turbulent area 28. The turbulence causes mixing of solids within the area 28. Solid particles within the area 28 may coagulate together. The coagulated particles may further coagulate with smaller solids which either get caught in the circulation currents of flow around the parallel plates (as described below) and are then either directed downwardly and returned to the reaction zone, or which may travel upwardly. Solids which travel upwardly through the coagulation area 28, then may settle out in the clarification zone, described further below, which is a quiescent zone, and will fall downwardly thus returning to the coagulation area 28 where the cycle may repeat until such time as the solids get caught in circulation currents of flow around the parallel plates and return to the reaction zone.

The coagulation area 28 is open at the top and in fluid communication with a liquid outlet 30 for removing separated liquids. The outlet may be in the form of a drain, an opening, a pipe, a conduit, a membrane hollow membrane preferably) or similar structures for withdrawing liquids. When installed in a upflow reactor apparatus such as the apparatus 12, it is preferred that a clarification zone 32 be provided between the coagulation area 28 and the liquid outlet 30, that the liquid be withdrawn from the clarification zone, and that the liquid level be maintained using either level controllers (not shown) and/or more preferably a system of overflow weirs 34 set to the appropriate level within the apparatus 12 as shown in FIG. 1.

Liquid may flow upwardly into the phase separator 10 either from a process having liquid and gas phases to be separated and/or a solid phase to be separated. If the separator is mounted within a single apparatus with a reaction zone as shown in the upflow reactor apparatus 12 of FIG. 1, liquid flows upwardly from an inlet 35 at the bottom of the apparatus 12 into the phase separator 10. In the case of an upflow reactor apparatus 12, such apparatus may have several different applications 30 and uses including aerobic and anaerobic waste water processing and the like. The upflow reactor apparatus 12, as well as the upflow reactors of the other embodiments described herein may be used in water treatment, physico-chemical wastewater treatment, biological wastewater treatment, food processing, the production of pharmaceuticals and other biotechnological applications. However, in the preferred embodiment described herein, the upflow reactor apparatus 12 is preferably for use in fermentation-type systems in which the solid is a biomass or other microbial culture and is introduced in the upflow reactor apparatus along with wastewater or another substrate or is resident in the reaction zone 50 thus contacting the liquid phase entering through inlet 55. In such systems, a biological reaction process such as fermentation is allowed to proceed, and there is typically a need to separate two or more phases, i.e., liquid, gas and/or solid.

Accordingly, as used herein an upflow reactor apparatus is any apparatus having a reactor in which liquid and gas, or solid, liquid and gas, or bulk content move in an upward direction through a portion of a reactor or throughout the entire cross section of the upflow reactor apparatus. With respect to wastewater treatment, such reactors may be applied for upflow anaerobic sludge blanket (UASB) processes, expanded granular sludge bed (EGSB) processes, fluidized bed (FB/UFB), processes gas-lift reactor processes, loop reactor processes, biological aerated filter (BAF) processes, and the like. In other biotechnological applications, such as the production of food products, fuel, ethanol or pharmaceuticals, such a reactor is generally referred to as a fermenter.

Preferably, the upflow reactor apparatus 12 is a fluidized bed, UASB, EGSB or similar process (referred to hereinafter generally as a "fluidized bed") apparatus for treatment of waste water using anaerobic fermentation. The solid biomass within such a system acts as a fermentation source and retention of the biomass is preferred within the reaction zone at the lower portion of the fluidized bed apparatus for as long as possible or to the maximum extent possible. Further, liquid entering the fluidized bed apparatus in such an application may not have a significant quantity of gas, however, gas generated within the fermentation process must be removed from the liquid in order to properly clarify and purify the treated waste water. While this is a preferred use for the phase separator and fluidized bed apparatus of the invention, it should be understood that the phase separator and fluidized bed apparatus could be easily adapted for other uses as described above in which the separation of a liquid and gas and/or a solid are important for the process and, preferably, in which a fluidized bed having an generally upwardly directed flow is useful.

Liquid flows into the coagulation areas 28 of each separation unit 14 through openings 36 which are located just to the left of the lower edges 38 of a series of parallel plates or baffles 40 within each separation unit 14 as shown in FIGS. 1, 4 and 8. The plates are inclined to the horizontal and vertical and are spaced from each other as shown in the Figures. It is preferred that there be at least two or more of such plates. However, any desired number which may practically fit into a separation unit within an existing upflow reactor apparatus is within the scope of the invention. Preferably, at least three such plates 40 are used as shown in the Figures. The uppermost plate 40 preferably adjoins the second wall 22 as shown best in FIGS. 1, 4 and 8. As used herein, each of the uppermost plates 40 of the separation units 14 "adjoin" walls 22 if the plates are connected to the walls 22 in a tightly fitting manner, are attached to, welded to or are a bent portion of the walls 22. Preferably, the uppermost plates 40 are fabricated to be bent portions of the walls 22.

Beneath the entrance 36 and below the lower edges 38 of each of the parallel plates 40 is preferably a deflector 42. As shown in FIGS. 1, 3, 4 and 8, each separation unit has a deflector 42. The deflector extends below and across the lower edges 38 of the parallel plates 40. The deflectors 42 preferably each adjoin the first walls 16 of the separation units in the same manner that the uppermost parallel plates adjoin the second walls. Most preferably, the deflector 42 is a bent portion of a prefabricated piece including the first wall 16. Each of the walls 16, 22, and plates 40, as well as the deflectors 42 extend transversely within the separation unit between two vertically extending walls 43 shown in FIG. 3. However, it will be understood that such walls could have modified configurations, i.e., sloped, curved and the like depending on the separation unit design, preferably such walls 43 are generally perpendicular with respect to the walls 16, 22.

Figure 6:
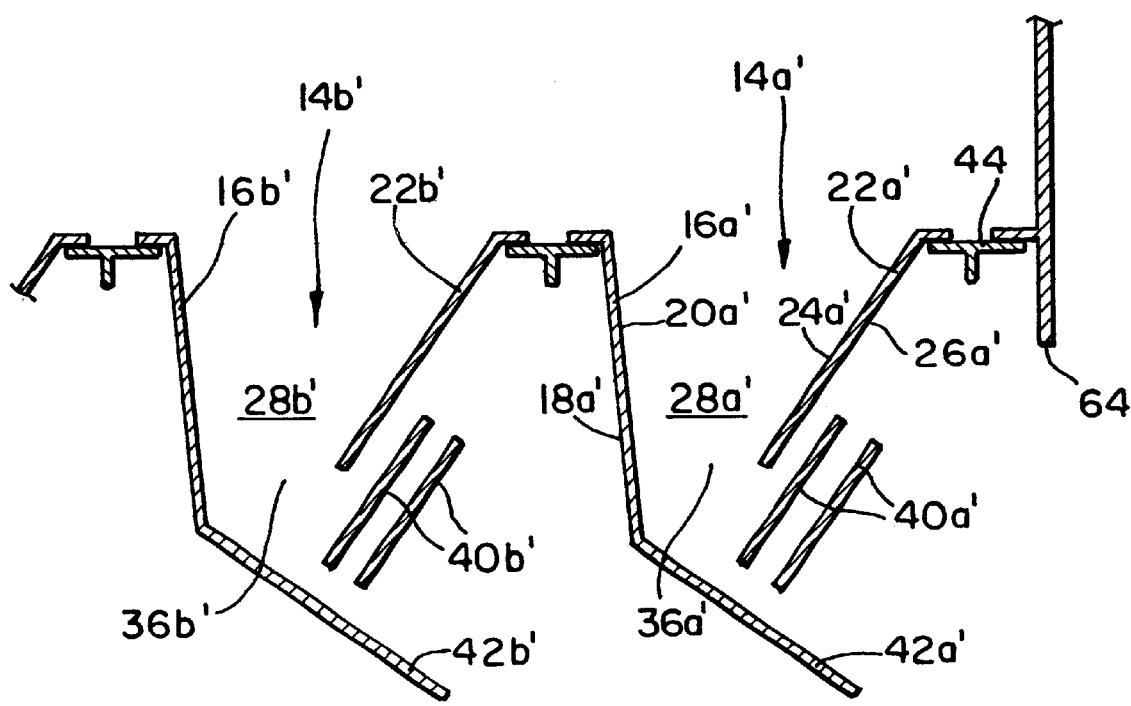
FIG. 6 is an enlarged cross sectional schematic representation of a further embodiment of phase separation units to be used within phase separators according to the invention.
Figure 7:
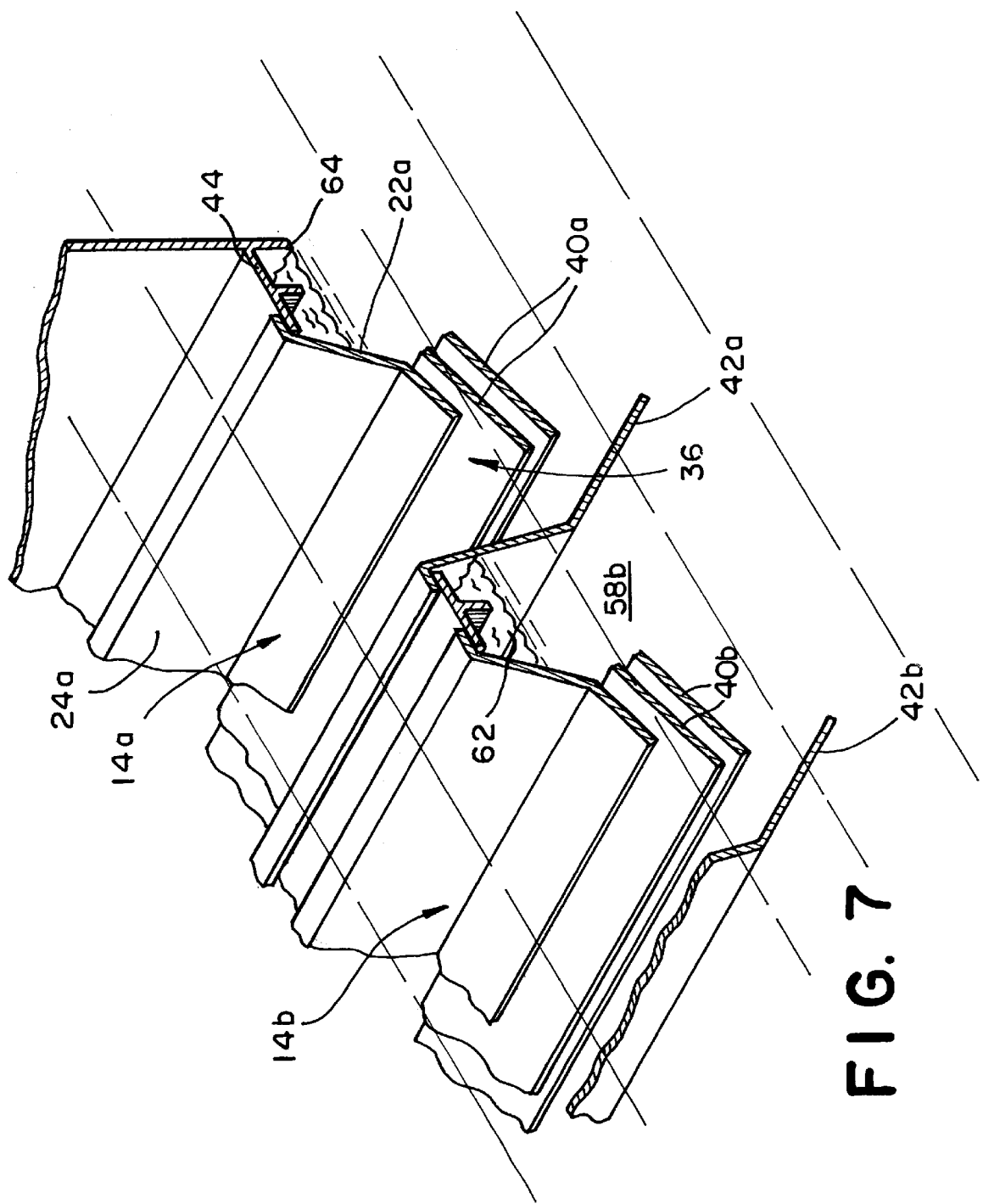
FIG. 7 is a perspective view of a phase separation unit within a phase separator according to the invention.

FIG. 6 illustrates an alternative embodiment of separation units 14' according to the invention in which the second wall 22a', 22b' of each unit is not bent and adjoins the uppermost parallel plate 40a', 40b' coextensively such that the two may be provided as a single plate.

Each separation unit is supported within an apparatus, such as an upflow reactor apparatus by a series of mechanical supports. Any suitable method of supporting or attaching prefabricated separation units 14 within an apparatus, such as an upflow reactor may be used. However, it is preferred that a series of support beams 44 in the form of a grid 46 be formed to which the walls 16, 22 of the separation units and the vertically extending walls 43 are attached. Such beams may be individual beams 44 or a single and complete panel with openings for the separation units 14. In any case, the support system must be secured to the separation units and be capable of blocking the flow of liquid coming through the separation units through any opening except for the openings 36.

The size of the upflow reactor apparatus 12 including a phase separator such as phase separator 10 according to the invention may vary depending upon the amount of influent liquid to be processed through the apparatus, the desired size of the reaction zone, the influent load and, in certain applications, the desired residence time and/or the amount of biomass desired within the reactor. It will be understood, based on this disclosure, that the phase separator 10 and upflow reactor apparatus 12, as well as the other variations described herein may be sized for different applications and that the height, width and other dimensions of the upflow reactor apparatus and phase separator may be varied accordingly by one skilled in the art. For an upflow reactor for use with anaerobic fermentation within the reaction zone using waste water influent, it is preferred that the reactor have a width or diameter, as measured transversely across the reaction zone of from about 1.2 m (4 ft.) to about 36.6 m (120 ft.), typically no greater than about 30.5 m (100 ft), and more preferably in the range of from about 2.4 m (8 ft.) to about 13.7 m (45 ft.). The reactor zone in such an apparatus would also preferably have a height, as measured longitudinally of from about 2.4 m (8 ft.) to about 24.4 m (80 ft.), more preferably from about 6.1 m (20 ft.) to about 18.3 (60 ft.).

The separation units preferably have a height to width ratio which ranges from about 4:1 to about 1:1, and more preferably from about 2:1 to about 1.3:1. The length of the separation units is generally limited in part by the strength of the materials of construction, but typically ranges from about 1.5 m (5 ft.) to about 15.2 m (50 ft.), where a preferred embodiment employs a modular approach including multiple units of standardized, equal length. In addition, the clarification zone has a transverse cross sectional area which varies from about 60% to about 200% of the transverse cross-sectional area of the reaction zone. The clarification zone further occupies a elevation or height measured in the longitudinal dimension of from about 15% to about 50% of the reactor elevation or height, more preferably from about 20% to about 35% of the reactor elevation.

Each of the separation units 14 may be arranged in various configurations within an existing apparatus depending on the degree of separation required, the space available within the apparatus design, the cross sectional geometry of the upflow reactor apparatus, and the selected size of each of the separation units. More units 14 of a smaller size can be used to provide a larger number of plates and more openings 36 overall within the same apparatus for a specified process requiring a high level of phase separation. In addition, the velocity parameters can be modified by increasing or decreasing the size and number of the separation units. Further, depending on whether the geometry of the apparatus in which the phase separator is to be used is circular or rectangular in cross section, the geometry can also dictate how many and in what arrangement the separation units are used. It is preferred that the size and number of separation units be determined so as to optimize the vertically and horizontally available space within a upflow reactor or other apparatus and to provide for optimal flow characteristics and an optimal clarification zone for effective solids separation.

The fluid upflow velocity in the reaction zone 50 ($V_r$) is generally established by the flow rate of the influent media and the cross sectional area of the reaction zone 50, and could be as high as 50 m/hr, whereas in biological treatment processes, it would more preferably be in the range of from about 2 to about 20 m/hr. For optimum solids retention, the separation units would be designed to provide an inlet velocity ($V_s$) which is not greater than about 10 times $V_r$, and more preferably which is from about 4 to about 6 times $V_r$. The upflow velocity in the clarification zone 32 ($V_c$) can be as high as about 70 m/hr, but more preferably is in the range of from about 2 to about 20 m/hr, and in the preferred embodiment in which maximization of solids retention is desired, $V_c$ is preferably in the range of from about 2 to about 8 m/hr. The upflow velocity of the gas in the reaction zone 50 ($V_g$) that is presented upon the separators is established by the fermentation process reaction and any supplemental introduction of reactive or inert gas, and typically may be up to about 40 m/hr, but is more preferably in the range of from about 2 to about 15 m/hr.

Further, it is preferred that the separation units are arranged in side-by-side configuration and in at least one transversely extending row to maximize the number of units which can be situated within a given apparatus. As shown in FIGS. 1 and 3, an exemplary upflow reactor apparatus 12 has a plurality of separation units 14 arranged side by side extending across the apparatus 12 and in two rows. The units may be aligned as shown in FIG. 3 or staggered in arrangement. However, aligned units are preferred since they provide the most efficient geometry and maximize the number of separation units which may fit within the apparatus.

The upflow reactor apparatus 12 of FIGS. 1 and 3 preferably also includes a gas collection chimney 48 which extends longitudinally within the upflow reactor apparatus. The chimney 48 is in fluid communication with a liquid intake portion of the upflow reactor apparatus. In the preferred instance of fermentation of a waste water intake, the liquid intake area would be a reaction zone 50 located at the bottom of the upflow reactor apparatus 12 below the phase separator 10. The reaction zone is preferably in liquid communication, indirectly, with the bottom of the gas collection chimney 48 by way of the gas collection area 58. The gas collection chimney 48 may be located in any gap within the support system of beams and/or grid of support or, preferably is located on one side of the upflow reactor apparatus 12 and separated from the phase separator by a wall 52. The wall 52 may be a single flat wall as shown in FIGS. 1 and 4 or may be a pipe or conduit provided liquid gas mixtures have no liquid outlet from the gas chimney. The gas collection chimney provides an area of free flow of all phases, but provides an outlet 54 only for gas. Accordingly, any other phases, combined with gas traveling up the gas collection chimney 48 would remain in the chimney and/or fall, flow or be drawn back into the reaction zone 50 or phase separator 10. It is preferred that a pressure regulator 68 or other pressure controller be provided to the apparatus 12 to control gas pressure within the top of the gas collection chimney. Such pressure control prevents the liquid level from rising so as to prevent liquid and/or solids from exiting by way of outlet 54.

Since it is preferred that the use of phase separation units 14 be maximized within the apparatus 12, it is preferred that the chimney, regardless of its configuration in cross section, i.e., regardless of whether it is circular, rectangular, triangular and the like, have a cross sectional area as measured transversely across apparatus 12 which is substantially less than the overall cross sectional area of the apparatus as best shown in the cross sectional representation in FIG. 3. Most preferably, in optimized designs, the gas collection chimney 48 should have a cross sectional area which is less than about 50%, more preferably from about 10% to about 40%, and most preferably from about 15% to about 25% of the overall cross sectional area of the reactor zone. In addition, it is preferred that the phase separation units 14 comprise at least about 50% more preferably from about 90% to about 60% and most preferably from about 85% to about 75% of the cross sectional area of the upflow reactor apparatus 12.

While such an arrangement is preferred with respect to the chimney 48 as described above, it is also within the scope of the invention to provide for an area of fluid communication such as a conduit (not shown) extending between the area above the clarification zone 32 and the gas head space 66. However, in such an embodiment, the clarification zone would also have to be enclosed and pressurized such that any gas which collects in that zone can be regulated and drawn off at outlet 54 which would be in fluid communication with an enclosed area (not shown) at the top of the clarification zone 32.

Further, while a gas chimney is a preferred outlet for gas collecting in gas-liquid interfaces which form in areas 58 between adjacent separation units 14, it will be understood to those of ordinary skill in the art that chimney 48 may be omitted in favor of a direct gas outlet 49 in fluid communication with the gas collection areas 58 such that gas in the top 62 of the collection areas 58 may pass outwardly through the outlet 49 which extends through the outer surface 51 of apparatus 10 as shown in phantom lines in FIG. 1. A direct gas outlet may include a pressure regulator 68' of the same type as pressure regulator 68. Such an outlet 49 may also be used in the other embodiments described further below. The outlet 49, while shown on one side of the upflow reactor apparatus 10, may be located at any point along the periphery of the upflow reactor apparatus provided the outlet is in fluid communication with the top 62 of gas collection areas 58.

The separation units 14 and the grid 46 or other support structure may be made of the same or different materials from each other or from the materials used to form the upflow reactor apparatus 12. Suitable materials of construction are materials which are preferably corrosion resistant metals and alloys (such as stainless steel and other similar alloys), polymeric materials, such as thermoplastic and thermosetting resins and elastomers, including fluorinated and perfluorinated materials (most preferably, polymers demonstrating a low level of water absorption or those having a water-resistant outer laminated coating), reinforced polymeric materials such as long- and short-glass fiber reinforced polymers, and ceramics. Advantages of use of polymeric and reinforced polymeric materials is the low cost of materials as well as the ease in formation. Further, such materials tend not to adhere to biomass in the case of use of the separator 10 in a fluidized bed apparatus having biomass. Stainless steel is also preferred for its corrosion resistance, and resistance to adhesion of biomaterials. Further, metals, such as steel which can be prefabricated are also preferred. It will be understood, based on this disclosure, that the material of construction is not critical to the overall design of the phase separator, and that the phase separation units and support structure as well as the entire upflow reactor apparatus having the phase separator may be prefabricated as separate pieces or as one piece without departing from the spirit of the invention.

The phase separator 10 and the phase separation units 14 are capable of separating a liquid and a gas, and preferably a solid in the manner best shown and explained with reference to FIG. 4. Liquid flowing upward to the area outside of the separation units 14 having a gas phase as shown by the schematic representation of open bubbles 56 will contact the deflectors 42 and the lower parallel plate 40. The gas bubbles will contact such surfaces and be diverted by them. As the gas is diverted in either direction, it will pass upwardly into gas collection areas 58 where it pools and collects in the gas collection pockets 62 at the top of the gas collection areas 58 forming a gas-liquid interface. As the gas rises around the right hand side of the lower most parallel plate 40, the liquid having the gas bubbles 56 to the right of the parallel plates 40 has a lower density than liquid which flows around the parallel plates 40 creating a density differential between the liquid around the parallel plates 40 and the gas-laden liquid to the right of the parallel plates in the gas collection areas 58. The differential in density causes a liquid circulation to occur around at least one of the parallel plates, preferably the outermost plate, while liquid flows generally in a downwardly directed flow around the innermost plates as shown in FIG. 4 leading liquid to the inlet 36 of each of the coagulation areas 28. Liquid entering the plates 40 or within the plates flows generally downwardly and at the entrance 36 of the coagulation area 28 will flow upwardly into the coagulation area due to the generally upward flow of liquid into the separation units from, for example, the use of an influent liquid pumping apparatus or similar upward liquid flow device. Preferably the liquid flowing within the innermost plates which is directed into the coagulation area is at a lower velocity and substantially devoid of gas in comparison with the velocity of liquid flowing around the outermost plate.

In the presence of particulates, such as biomass, designated by a schematic representation using solid dots 60 in FIG. 4, the solid particulate will flow with some of the liquid through the parallel plates, and be drawn generally downwardly by gravity and the downwardly directed flow within the plates 40. At the same time, substantial amounts of liquid without gas and with some particulate will continue to pass generally upwardly into the coagulation area 28. Solids in this area further coagulate due to turbulence caused in part by upward and downward flow patterns resulting from upwardly moving particles and downwardly moving coagulated particles which fall downwardly out of the separator, and preferably to a reaction zone of an upflow reactor apparatus. Once the particulate 60 contacts the deflector and/or exits the lower edges 38 of the plates, it is directed generally downwardly by the deflector and gravity out of the separator and preferably, in an upflow reactor apparatus, downwardly into a reaction zone 50. The flow at the base of the deflector, which also experiences a differential in density from the upwardly flowing liquid into the coagulation area 28, and the gas-laden liquid in the gas collection areas 58 is further drawn down by the liquid circulation created by the density differential.

In separating and directing gas out of the separator, gas will continue to collect at the top 62 of the gas collection areas 58 until the ongoing upwardly flowing liquid within the separator and/or upflow reactor apparatus having the separator force the gas transversely along the lower portion of the separator, unit by unit to the path of least resistance for the gas, which is either to a direct off-take outlet 49 or preferably until it passes under the lower edge 64 of the wall 52 forming a gas collection chimney. It will then bubble up through the gas collection chimney to the space 66 at the top of the chimney. Gas is then removed and/or collected from the outlet 54, preferably through a controller or pressure regulator 68 as shown in FIG. 1. Such a controller may be manually or computer controlled, and any suitable controller may be used which is capable of regulating gas flow. It will be understood by one of ordinary skill in the art, that backup valves or pressure regulating valves and various systems may be used in connection with the gas outlet as are known or to be developed within the art, provided the control and/or regulating system is capable of maintaining sufficient pressure within space 66 to maintain the desired liquid level.

All phases, gas and liquid, or gas, solid and liquid, may enter the gas collection chimney, but only gas is permitted to exit the chimney through outlet 54. Liquid is maintained within the chimney by use of pressure on the upper liquid level to maintain the space 66. Particulates, if any, which may be present within the gas collection chimney by being drawn up into the chimney by gas or liquid turbulence caused by rising gas bubbles and/or the rising and falling of solids tend to fall with gravity to the reaction zone 50 or below the phase separator 10.

As described above, the phase separator may be used to separate only liquid and gas, or to separate three phases, solid, liquid and gas depending upon the use of the phase separator in a particular application. As the only path to an exit for liquid flowing upward within an upflow reactor apparatus or other similar apparatus having the phase separator is upward, the liquid is forced to pass through the phase separator and must enter through inlets 36. As such, the only liquid communication between the area below the phase separator, such as reaction zone 50 and the area above the phase separator 10, such as clarification zone 32 is through the inlets 36 and, accordingly, through the coagulation areas 28. Once within the coagulation areas 28, while a significant portion of particulate has already been drawn downwardly into the reaction zone by the phase separator, any particulate which may have passed with the liquid into the coagulation areas 28 will tend to eventually coagulate and settle out by gravity in the coagulation areas and be directed downwardly out of the separator, and preferably to a lower portion of the apparatus having the phase separator, such as to a fermentation reaction zone 50. It is further preferred that an additional clarification zone such as clarification zone 32 be provided for additional settling of fine particulate which did not coagulate or otherwise settle out from the coagulation areas 28.

By providing the phase separator below such a clarification zone and blocking off the entire transverse cross sectional area with the exception of the gas collection chimney or other gas outlet, the clarification zone 32 or other collection area on top of the coagulation areas 28 has a sufficiently low turbulence and liquid velocity to allow for a high degree of settlement of remaining fine particulate allowing for a higher level of solids retention and better clarification. The design of the separation units 14 allows for the maximization of the number of separation units which may be provided to an upflow reactor apparatus thereby increasing the potential for solids retention and improving flow characteristics. Since there are at least two, and preferably a multiple number of such separation units 14 extending transversely within an apparatus such as an upflow reactor apparatus, a lower upward fluid velocity can be maintained and a smaller velocity differential between upwardly and downwardly directed flow is maintained. In addition, there are a larger number of inlets into the coagulation areas, in which flow is turbulent creating enhanced ability for solids to coagulate and fall downwardly into the reaction zone. Further, the degree of velocity increase at the openings 36 is minimized and the velocity differential reduced at the separator entrances causing better and more efficient separation of phases, and increased retention of solids. The design of the phase separator also allows for a maximized clarification zone since gas can be deflected at the gas-liquid interface which occurs between separation units and below the clarification zone.

Figure 2:
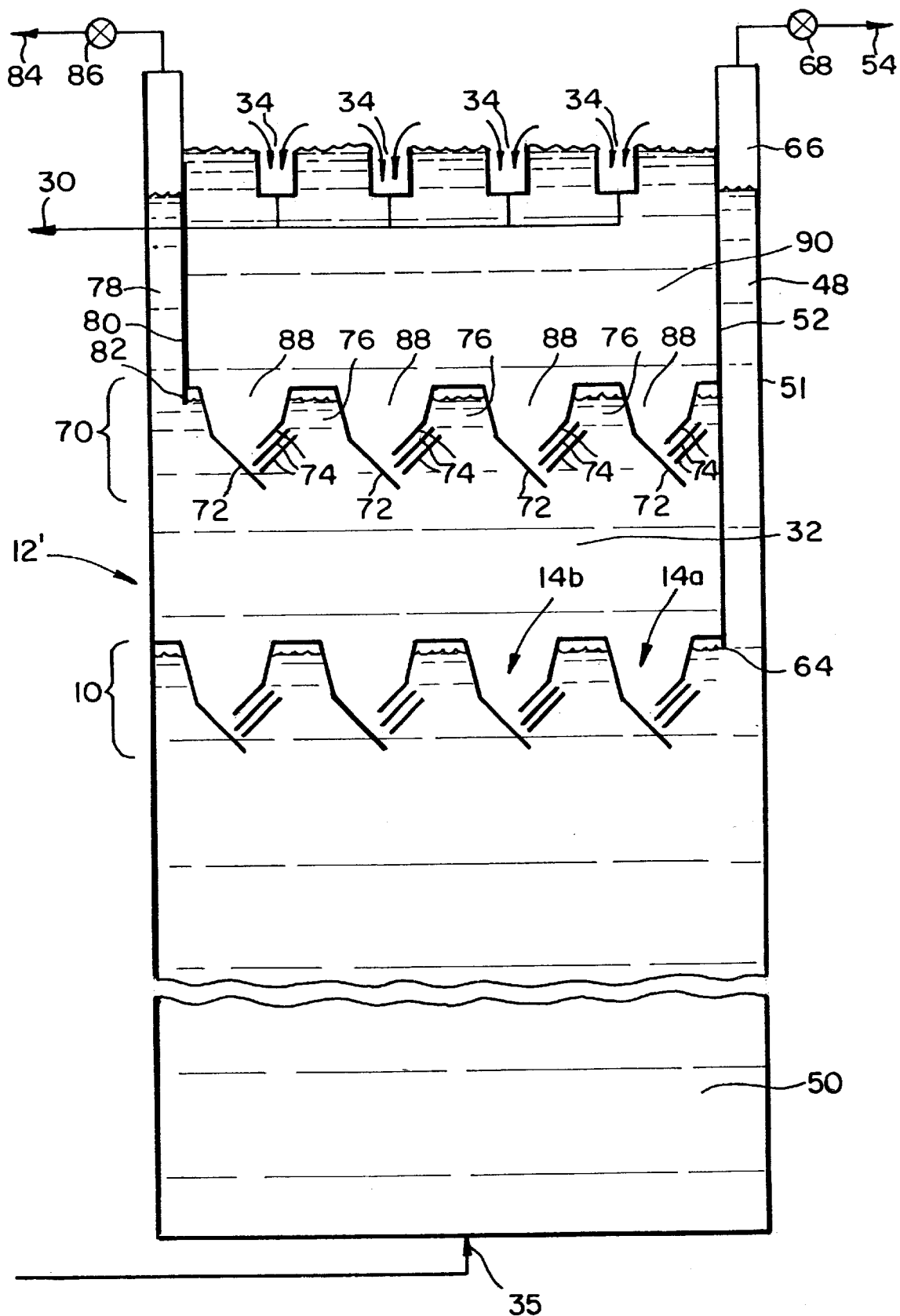
FIG. 2 is a cross sectional schematic representation of an upflow reactor apparatus with multiple phase separators according to the invention.

FIG. 2 shows an alternative embodiment of an upflow reactor apparatus 12' of the invention in which two phase separators 10 according to the invention are arranged in series. While it will be understood, based on this disclosure, that the phase separator is highly efficient when used alone, in the event of a need for an even higher degree of separation efficiency in certain applications, or if there is a desire for even higher solids retention, for example, for high biomass retention in a reaction zone of a fermentation fluidized bed, it may be desirable to use two such devices in series horizontally as shown.

In FIG. 2, an upflow reactor apparatus 12' is shown which has a second multiple unit phase separator 70 shown on top of and longitudinally spaced from (that is, separated from in a longitudinal direction) a phase separator 10 that is the sane as the phase separator 10 of FIG. 1 and as described above. Phase separator 70 is preferably identical to, but may be slightly modified in size or configuration if desired with respect to the phase separator 10 as described above. Liquid passing upwardly from the first phase separator 10 will first pass through a first clarification zone 32. In the event solid and/or gas remains or is generated in the clarification zone 32, and the solid is reactive such as in an anaerobic purification/fermentation process in which some biomass reaction and/or additional gas generation can occur or can be caused to occur such as by a reaction with a catalyst or other initiator, the clarification zone 32 may also function in the manner of a lesser reaction zone. Gas which may generate in zone 32 will be diverted by the deflectors 72 and lowermost parallel plates 74 of each of the phase separation units 71 of the phase separator 70 into gas collection areas 76 in the same manner in which the phase separator 10 functions.

Gas which collects in areas 76 may either be removed by providing an intake only opening (not shown) into the gas collection chimney in which gas can be drawn upwardly into the chimney 48, by providing a direct gas outlet such as gas outlet 49, or, more preferably, by providing a second gas collection chimney 78 at another location in the apparatus 12', such as on the opposite side of the apparatus 12' from chimney 48. By using this configuration, a high integrity in keeping gas-laden liquid and/or solids within chimney 48 and not in area 32 can be maintained. The second chimney 78 may be formed with a wall 80 extending up the opposite side of the apparatus and extending downwardly to provide a lower edge 82 under which any gas collecting in gas collection areas 76 can pass to exit through chimney 78. The gas may pass outwardly from apparatus 12' through an outlet 84 at the top of the chimney which is preferably regulated by a controller or pressure regulator 86 in the same manner as in gas chimney 48 and outlet 54. The chimney 78 preferably has dimensions similar to, and preferably equal to or less than the dimensions of chimney 48.

Once the separated liquid passes upwardly through coagulation areas 88 of the phase separation units 71 of phase separator 70, it is preferably directed to a second clarification zone 90 in which any remaining particulate may be directed downwardly by gravity into the coagulation areas 88 and directed along deflectors 72 to clarification area 32 and so forth as described in detail above down to reaction zone 50.

Figure 5:
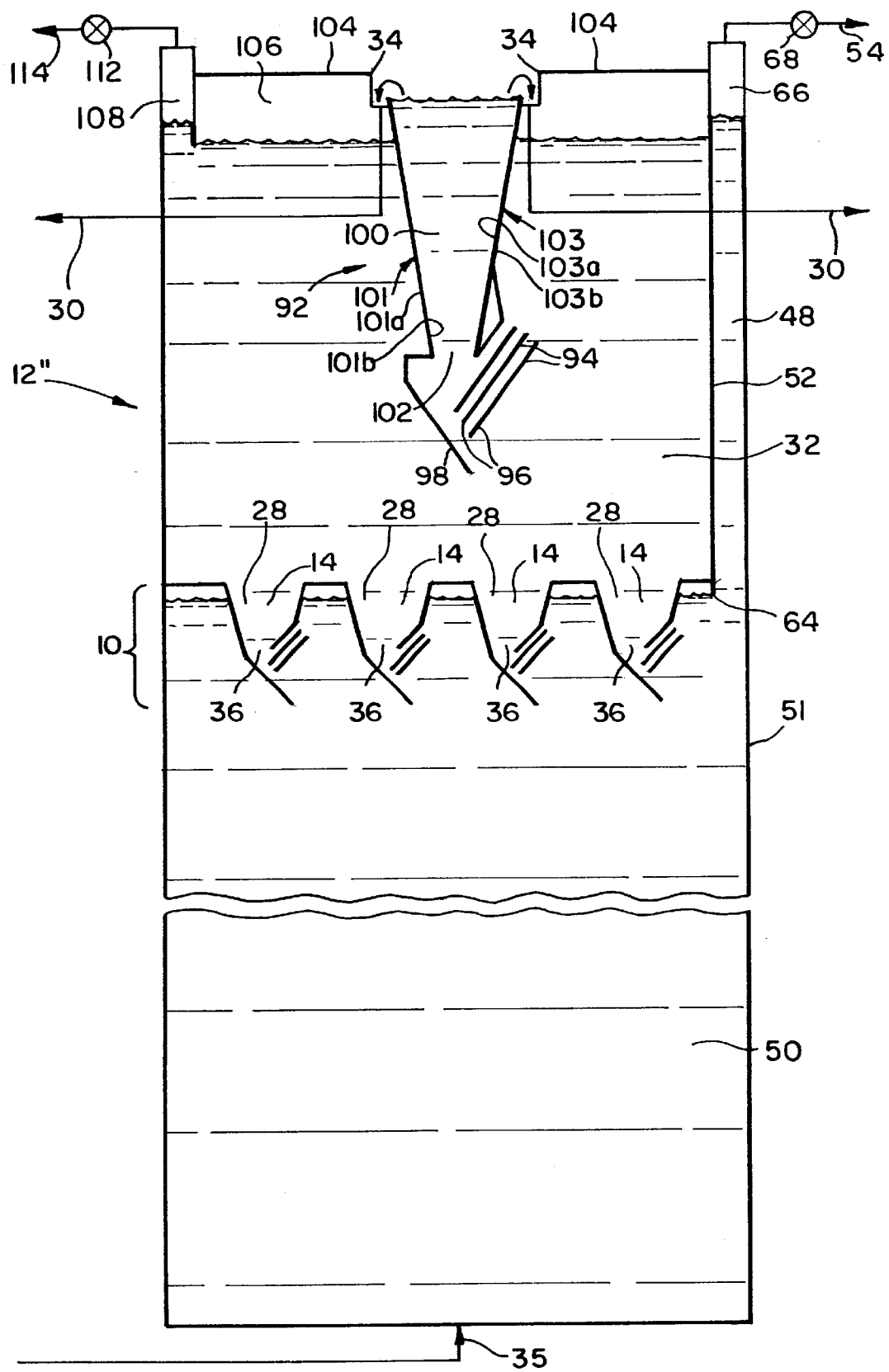
FIG. 5 is a cross sectional schematic representation of an upflow reactor apparatus with multiple phase separators in accordance with a further embodiment of the invention.

The phase separator 10 of the invention may be used alone or with a second separator separated from the phase separator 10 longitudinally. Such second separator may be a phase separator in accordance with the invention and located in series as discussed above with respect to the combination of phase separator 10 and phase separator 70 which includes multiple separation units. While the second separator may be the same as the phase separator 10 of the invention, the second separator may be a separator which is different from the phase separator 10. An upflow reactor apparatus 12" having a second separator 92 in series with a phase separator 10 in accordance with the invention is shown in FIG. 5. The phase separator 92 is made in accordance with the description of U.S. Pat. No. 5,855,785, the entire disclosure of which is incorporated herein by reference. The separator 92 has a series of parallel plates 94 inclined to the horizontal and vertical and spaced apart as shown in FIG. 5 and are similar to the parallel plates 40 in the separation units 14. The parallel plates 94 have lower edges 96 that lie to the right of and are spaced from a deflector 98. Liquid passing upward from clarification zone 32 enters the plates 94 and by differential flow and using gas lift circulation the liquid is drawn through the plates 94 and into the settling area 100. The second separator has a first wall 101 having a first side 101a and a second side 101b and a second wall 103 having a first side 103a and a second side 103b. The walls 101 and 103 may be flat, extending angled walls or can be curved together to form a conical unit without departing from the spirit of the invention. Regardless of the shape of the walls 101, 103, the walls define the settling area 100. Liquid enters the settling area 100 through opening 102. While the cross section of available opening 102 into the second separator 92 is smaller than the overall combined cross sectional areas of the openings 36 into coagulation areas 28, the overall amount of remaining particulate in liquid entering the second separator 92 should be very low. Further, the velocity in the clarification zone is preferably low such that the increase in liquid velocity through opening 102 can be minimized.

The use of a second separator 92, while not necessary, functions to help ensure a high level of efficiency in separation. The liquid exiting the overflow at the top of separator 92 is removed by way of overflow weirs 34. The weirs are mounted to an upper plate 104 which covers the top of the remaining portion of the upflow reactor apparatus and which allows for any collected gas to be directed into the area 106 below the plate 104 and above the upper liquid level within the upflow reactor apparatus. The level is preferably maintained in the same manner as described above and as shown and described for the upflow reactor apparatuses shown in FIGS. 1 and 2. Preferably, a second gas collection chimney 108 is provided with a lower edge 110 that may be used to regulate collection of gas and the liquid level in combination with a pressure controller and/or regulator 112 that controls the amount of gas removed by gas outlet 114. Liquid is removed by one or more drains, conduits, pipes, membranes and the like which are in communication with one or more liquid outlets 30.

The design of FIG. 5 is preferably used for applications in which it is desired to improve performance of an existing system by providing an additional layer of separation units below an existing separator(s) to provide improvements in flow characteristics and improve clarification of suspended solids. It will also be understood, based on this disclosure, that the design of FIG. 5 can be reversed such that a phase separator such as phase separator 10 is located above a separator such as separator 92 in FIG. 5 within the scope of the invention in order to modify an existing apparatus having a separator such as separator 92. In such an instance, a phase separator such as phase separator 10 according to the invention would be fitted above a separator such as separator 92 within an existing apparatus. It should be understood that in reversing such a design as shown in FIG. 5, that weirs such as the weirs shown in FIG. 2 would be provided above a clarification zone 32 which is above phase separator 10 (in the manner shown in FIG. 2). Further, chimney 108 in FIG. 5 would be in fluid communication with gas collection areas between the separation units 14 and chimney 48 would then be in fluid communication with a gas collection area that would be formed using a plate such as plate 104 at a lower location in the apparatus and extending from an upper portion of the lower separator 92.

The invention also includes a method of separating a liquid and a gas within an upflow reactor apparatus having a reaction zone. The method includes providing an upflow of liquid and gas, and optionally solid, within the upflow reactor apparatus. The upflow of liquid and/or solid may be provided from a number of sources, including waste water treatment, reaction mixtures and the like. Preferably, the reaction zone is an anaerobic fermentation reaction zone, the liquid is waste water, a solid phase is present in the form of a biomass and gas is generated within the reaction zone during fermentation. The gas may be within a mixture of inflowing liquid and/or solid or may be generated within the reaction zone of the upflow reactor apparatus in the manner in which a gas is generated in an anaerobic purification of waste water.

The upflowing liquid and gas and/or solid flow upwardly into a phase separator having a series of parallel plates which must be encountered prior to liquid entering the main portion of the phase separator, preferably the phase separator 10 having at least two separation units 14 as shown in FIGS. 1, 3, 4 and 7. However, it will be understood based on this disclosure, that the preferred embodiments of the method may be practiced using other separator combinations described herein, including the use of more than one multiple separation unit phase separator such as phase separator 10 in series as shown in FIG. 2, or the use of a multiple unit phase separator such as phase separator 10 below a further separator device, such as separator 92 as shown in FIG. 5 or above such a separator 92 as discussed above. It is preferred that while any suitable phase separator can be used within the scope of the method of the invention having parallel plates situated prior to entry into the main body of the separator, that the phase separator 10 alone or in combination with an upper separator such as a further phase separator 10 or a separator 92 as described in detail above be used and adapted in the method of the invention.

Once the upflow of liquid encounters the lower portion of the phase separator, a liquid circulation is provided around at least one of a series of parallel plates, the lowermost of which diverts gas away from the parallel plates thereby contributing to a fluid density differential and a liquid circulation around the parallel plates. Preferably the phase separator has a gas collection area for collecting gas diverted by the parallel plates, such as the gas collection areas 58. The liquid circulation contributes to a generally downwardly directed flow around the parallel plates such that liquid separated from the gas can be directed away from the gas collection area and into coagulation areas 28. The downwardly directed flow of liquid around the plates will encounter generally upflowing liquid within the upflow reactor apparatus and either be directed upward into the phase separator to a liquid collection area, preferably a coagulation area such as coagulation areas 28 and the like as described above, or some of the liquid may continue its downwardly directed flow toward the reaction zone until it encounters further upflowing liquid which changes the direction of flow. It is further preferred that clarified liquid exiting the phase separator is removed from a liquid outlet, and more preferably that it is removed from a liquid outlet after passing through a clarification area above the phase separator to enable any remaining particulate to descend by gravity into the coagulation area of the phase separator and ultimately to be directed downwardly into the reaction zone.

The gas diverted by the parallel plates is then collected in the gas collection areas, such as gas collection areas 58 and directed to a gas outlet which is preferably also accomplished in any of the gas removing systems described above.

It is preferred that the method further provides for the separation of a solid phase from the liquid and gas phases. Solid in the reaction zone may be kept substantially within the reaction zone to increase solid residence time in the case of reactive solids or to further separate and remove through the bottoms of the upflow reactor apparatus for undesirable solids by using the method of the invention. Solids which flow upwardly due to the upflow of liquid and gas within the reaction zone generally contact the lowermost parallel plates, and more preferably also contact deflector plates such as deflector plates 42 to divert some of the solid downwardly by gravity. However, the general upflow of liquid and remaining solid will contact the lowermost parallel plate and, when the gas flow is diverted to a gas collecting area, will be drawn into the parallel plates due to the liquid circulation created by the density differential. The downflow of liquid and solid within and around the plates will then allow the solid to be directed downwardly along a deflector or deflectors such as the deflectors 42 into the reaction zone or upwardly into coagulation zone 28 at the inlet 36.

The method of the present invention using the preferred phase separator 10 of the present invention can provide very favorable retention of solids within the upflow reactor for use in systems such as anaerobic fermentation of waste water. In such a preferred embodiment, the reaction zone is sized so as to provide for a chemical oxygen demand (COD) reduction of from about 50% to about 95% based on the relationship of available COD to the biomass volume present in the reaction zone, and more typically in the range of from about 70% to about 92% COD. The diameter and height of the reaction zone may be adjusted based on the COD available in the waste water so as to achieve the preferred hydraulic upflow velocity $V_r$ and the preferred gas velocity $V_g$ for the gas volume generated by the digestion of the COD. In such an embodiment, it is preferred to optimize solids retention in the reactor zone. The separation units thus are adjusted in size and quantity to obtain the lowest preferred separator inlet velocity $V_s$. The upflow velocity in the clarification zone $V_c$ is preferred to be no more than about 35% of the settling rate of the solids desired to be retained, typically in the range of from about 2 to about 30 m/hr, and more preferably in the range of from about 2 to about 10 m/hr. The width or diameter of the clarification zone can be adjusted as necessary to achieve the preferred result.

The invention also includes a method of separating a liquid and gas within an upflow reactor apparatus having a reaction zone and having a first phase separator located above the reaction zone and below a second separator. The reaction zone is preferably, but not necessarily, an anaerobic fermentation reaction zone such that the liquid phase would be waste water and gas can be generated within the reaction zone or dissolved in and/or mixed within the waste water phase entering the upflow reactor through the liquid inlet. In such a preferred embodiment, solid phase is also present for separation in the form of biomass and it is desirable to retain the biomass for as long as possible within the reaction zone.

The method includes providing an upflow of liquid and gas and/or solid within the upflow reactor apparatus such that the liquid and gas flow from the reaction zone upwardly into a first separator. The first separator has at least one phase separation unit such that it could be a multiple unit phase separator 10 or a separator such as separator 92. It will be understood based on this disclosure, that in the preferred embodiment of the method, a separator such as separator 92 is preferably located above a multiple unit phase separator such as phase separator 10 having at least two phase separation units. It is further preferred that the lower separator and the upper separator each have at least one plurality of parallel inclined plates such as plates 40, 94, 94a and a deflector which extends downwardly and below such plates such as deflectors 42, 98.

Liquid circulation is provided around the parallel plates by using the parallel plates and/or the deflectors to divert gas away from the liquid collection area, such as the coagulation areas 28 or settling area 100 and into a gas collecting areas such as areas 58 or area 118. The diversion of such gas operates as discussed above and creates a liquid density differential between liquid inside the plates and liquid outside the plates laden with diverted gas thereby creating a liquid circulation around the plates. The liquid circulation provides a downwardly directed flow around the parallel plates of the first separator and enables liquid to be directed generally from the bottom of the plates up into a coagulation area or other liquid collection area using the generally upward flow of the upflow reactor apparatus, or in the event solids are present, to direct solids downwardly using the downward flow through the plates and/or gravity as the solids contact the deflector.

The diverted gas is preferably directed from a gas collecting area to an outlet from the upflow reactor apparatus. Liquid from the liquid collection area, such as a coagulation area is directed upwardly using the upward velocity of the upflow reactor apparatus into a second separator. The second separator, as discussed above, may be a separator such as separator 92 or is preferably a multiple unit phase separator such as separator 10 described in detail above. Liquid is then removed from the upflow reactor apparatus using an outlet above the second separator. Preferably, before entering the second separator, liquid passes through a clarification zone, which if any biomass is still present, may include some reaction within the zone and gas generation depending on the type of activity. When using a multiple phase separator such as phase separator 10 as the second separator, a further clarification zone above the second separator and in liquid communication with the second separator, such as clarification zone 90 of FIG. 2 can also be provided to the upflow reactor apparatus for further clarification of the liquid within the upflow reactor apparatus prior to removing clarified liquid.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A phase separator capable of being used with an upflow reactor apparatus and comprising a first separation unit and a second separation unit, each of the first and the second separation units comprising
   (a) a first wall having a first side and a second side and a second wall having a first side and a second side, the second side of the first wall and the first side of the second wall defining a coagulation area, wherein the first wall adjoins a deflector inclined to the horizontal and vertical; and
   (b) a plurality of parallel plates spaced from each other and vertically and horizontally inclined, each of the parallel plates having a lower edge, wherein the second wall adjoins one of the parallel plates and the deflector extends below and across the lower edges of the parallel plates, wherein each of the first and the second separation units is capable of separating a gas from a liquid by diverting the gas to the second side of the second wall of each separation unit and by creating a circulation of the liquid around at least one of the parallel plates such that liquid is directed into the coagulation area.

2. The phase separator according to claim 1, wherein the phase separator is a three-phase separator and is further capable of separating a gas and a liquid from a solid by directing the solid downwardly along the deflector while the liquid passes into the coagulation area.

3. The phase separator according to claim 1, wherein the first separation unit and the second separation unit are arranged such that the second side of the second wall of the first unit and the first side of the first wall of the second unit define a gas collection area.

4. The phase separator of claim 1, wherein the phase separator comprises greater than two separation units, each separation unit having
   (a) a first wall having a first side and a second side and a second wall having a first side and a second side, the second side of the first wall and the first side of the second wall defining a coagulation area, wherein the first wall adjoins a deflector inclined to the horizontal and vertical; and (b) a plurality of parallel plates spaced from each other and vertically and horizontally inclined and each of the parallel plates having a lower edge, wherein the second wall adjoins one of the parallel plates and the deflector extends below and across the lower edges of the parallel plates, wherein each of separation units is capable of separating a gas from a liquid by diverting the gas to the second side of the second wall of each separation unit and by creating a circulation of the liquid around at least one of the parallel plates such that liquid is directed into the coagulation area.

5. The phase separator according to claim 4, wherein the plurality of separation units are arranged in at least one transversely extending row and wherein the separation units within each of the at least one transversely extending row are arranged such that a gas collection area is formed between adjacent separation units.

6. An upflow reactor apparatus, comprising a phase separator, wherein the phase separator comprises a first separation unit and a second separation unit secured within the upflow reactor apparatus, each of the first and the second separation units comprising (a) a first wall having a first side and a second side and a second wall having a first side and a second side, the second side of the first wall and the first side of the second wall defining a coagulation area, wherein the first wall adjoins a deflector inclined to the horizontal and vertical; and (b) a plurality of parallel plates spaced from each other and vertically and horizontally inclined, each of the parallel plates having a lower edge, wherein the second wall adjoins one of the parallel plates and the deflector extends below and across the lower edges of the parallel plates, wherein each of the first and the second separation units is capable of separating a gas from a liquid by diverting the gas to the second side of the second wall of each separation unit and by creating a circulation of the liquid around at least one of the parallel plates such that liquid is directed into the coagulation area.

7. The upflow reactor apparatus according to claim 6, further comprising a liquid clarification zone above the first and second separation units.

8. The upflow reactor apparatus according to claim 6, wherein the phase separator is situated on top of a reaction zone within the upflow reactor apparatus.

9. The upflow reactor apparatus according to claim 6, wherein the phase separator is a three-phase separator and is further capable of separating a gas and a liquid from a solid by directing the solid downwardly along the deflectors while the liquid passes into the coagulation area.

10. The upflow reactor apparatus according to claim 9, wherein the upflow reactor apparatus further comprises a reaction zone and is capable of anaerobic fermentation of waste water liquid in which a gas is generated within the reaction zone and the waste water liquid further comprises a biomass solid for returning to the reaction zone.

11. The upflow reactor apparatus according to claim 6, wherein the first separation unit and the second separation unit are arranged such that the second side of the second wall of the first separation unit and the first side of the first wall of the second separation unit define a gas collection area and the gas collection area is in fluid communication with a gas outlet extending outwardly through an outer surface of the upflow reactor apparatus.

12. The upflow reactor apparatus according to claim 6, further comprising a clarification zone on top of the first separation unit and the second separation unit and in liquid communication with the coagulation areas, and a reaction zone below the first separation unit and the second separation unit, wherein the only liquid communication between the reaction zone and the clarification zone occurs through the coagulation areas of the first and the second separation units.

13. The upflow reactor apparatus according to claim 12, further comprising a gas collection chimney extending longitudinally within the upflow reactor apparatus and having a gas outlet and an area as measured in the transverse direction which is substantially less than a cross sectional area of the upflow reactor apparatus, wherein the gas collection chimney is in liquid communication with the reaction zone.

14. The upflow reactor apparatus according to claim 13, wherein the cross sectional area of the gas collection chimney is from about 10% to about 40% of the cross sectional area of the upflow reactor apparatus.

15. The upflow reactor apparatus according to claim 6, wherein the phase separator comprises a plurality of separation units each having (a) a first wall having a first side and a second side and a second wall having a first side and a second side, the second side of the first wall and the first side of the second wall defining a coagulation area, wherein the first wall adjoins a deflector inclined to the horizontal and vertical; and (b) a plurality of parallel plates spaced from each other and vertically and horizontally inclined and each of the parallel plates having a lower edge, wherein the second wall adjoins one of the parallel plates and the deflector extends below and across the lower edges of the parallel plates, wherein each of separation units is capable of separating a gas from a liquid by diverting the gas to the second side of the second wall of each separation unit and by creating a circulation of the liquid around at least one of the parallel plates such that liquid is directed into the coagulation area.

16. The upflow reactor apparatus according to claim 15, wherein the plurality of separation units are arranged in at least one transversely extending row and wherein the separation units within each of the at least one transversely extending row are arranged such that a gas collection area is formed in between adjacent separation units and the gas collection areas are in fluid communication with at least one gas outlet.

17. The upflow reactor apparatus according to claim 15, wherein the plurality of separation units are arranged transversely across a portion of a cross-sectional area of the upflow reactor apparatus and the upflow reactor apparatus further comprises a gas collection chimney extending longitudinally within the upflow reactor apparatus and having a gas outlet.

18. The upflow reactor apparatus according to claim 17, wherein the plurality of separation units comprise from about 60% to about 90% of the cross sectional area of the upflow reactor apparatus and the gas collection chimney has a cross sectional area as measured in the transverse direction which comprises from about 10% to about 40% of the cross sectional area of the upflow reactor apparatus.

19. The upflow reactor apparatus according to claim 17, further comprising a pressure controller for the gas outlet which regulates a pressure of collected gas at a top of the gas collection chimney.

20. The upflow reactor apparatus according to claim 15, further comprising a clarification zone on top of and in liquid communication with each of the coagulation areas of the separation units, wherein the clarification zone comprises a liquid outlet for clarified liquid.

21. The upflow reactor apparatus according to claim 15, further comprising at least one second separator which may be the same or different from the phase separator, wherein the at least one second separator is situated on top of the phase separator within the upflow reactor apparatus.

22. The upflow reactor apparatus according to claim 21, wherein the at least one second separator is the same as the phase separator and the at least one second separator is longitudinally spaced from the phase separator.

23. An upflow reactor apparatus comprising a first phase separator and a second separator which may be the same or different from the first phase separator, wherein the at least one second separator is located on top of and longitudinally spaced from the first phase separator within the upflow reactor apparatus, wherein at least one of the first phase separator or the second separator comprises a first separation unit and a second separation unit secured within the upflow reactor apparatus, each of the first and the second separation units comprising:
(a) a first wall having a first side and a second side and a second wall having a first side and a second side, the second side of the first wall and the first side of the second wall defining a coagulation area, the first wall adjoining a deflector inclined to the horizontal and vertical; and
(b) a plurality of parallel plates spaced from each other and vertically and horizontally inclined, each of the parallel plates having a lower edge, the second wall adjoining one of the parallel plates and the deflector extending below and across the lower edges of the parallel plates.

24. The upflow reactor apparatus according to claim 23, wherein the at least one second separator is the same as the first phase separator.

25. The upflow reactor apparatus according to claim 23, further comprising a reaction zone below the first phase separator, a first clarification zone located between the first phase separator and the second separator, and a second clarification zone above the second separator.

26. The upflow reactor apparatus according to claim 25, further comprising a gas collection chimney in liquid communication with the reaction zone, wherein the gas collection chimney has a cross sectional area measured in the transverse direction which is substantially smaller than a cross sectional area of the upflow reactor apparatus.

27. A method of separating a liquid and a gas within an upflow reactor apparatus having a reaction zone, comprising
(a) providing an upflow of liquid and gas within the upflow reactor apparatus such that the liquid and gas flow upwardly from the reaction zone into a phase separator having a first separation unit and a second separation unit, wherein each of the first and the second separation units have (i) a first wall having a first side and a second side and a second wall having a first side and a second side, the second side of the first wall and the first side of the second wall defining a coagulation area, the first wall adjoining a deflector inclined to the horizontal and vertical and (ii) a plurality of parallel plates spaced from each other and vertically and horizontally inclined, each of the parallel plates having a lower edge, the second wall adjoining one of the parallel plates and the deflector extending below and across the lower edges of the parallel plates;
(b) providing a liquid circulation around at least one of the parallel plates by diverting gas flow to a gas collecting area between the second side of the second wall of the first separation unit and the first side of the first wall of the second separation unit such that the liquid circulation provides a downwardly directed flow around the parallel plates of each of the first and the second separation units and liquid is directed toward the coagulation area; and
(c) directing the diverted gas from the gas collecting area out of the upflow reactor apparatus through a gas outlet.

28. The method according to claim 27, further comprising separating a solid from the liquid and the gas by directing the solid downwardly along the deflectors to the reaction zone.

29. The method according to claim 28, wherein the reaction zone is an anaerobic fermentation reaction zone.

30. The method according to claim 29, wherein the liquid is waste water, the solid is biomass and the gas is generated within the reaction zone.

31. The method according to claim 27, further comprising removing clarified liquid from a clarification zone in liquid communication with the coagulation areas and above the phase separator.

32. The method according to claim 31, wherein a fluid upflow velocity in the clarification zone is no greater than about 70 m/hr.

33. The method according to claim 32, wherein the fluid upflow velocity in the clarification zone is from about 2 m/hr to about 20 m/hr.

34. The method according to claim 27, wherein a fluid upflow velocity in the reaction zone is no greater than about 50 m/h.

35. The method according to claim 34, wherein the fluid upflow velocity in the reaction zone is from about 2 to about 20 m/hr.

36. The method according to claim 27, wherein an inlet velocity to the first and second separation units is not greater than about 10 times a fluid upflow velocity in the reaction zone.

37. The method according to claim 36, wherein the inlet velocity to the first and second separation units is from about 4 to about 6 times the fluid upflow velocity in the reaction zone.

38. The method according to claim 27, wherein a gas upflow velocity in the reaction zone is not greater than about 40 m/h.

39. The method according to claim 27, wherein step (a) further comprises directing the upflow of liquid and gas through an additional separator which may be the same or different from the phase separator and which is above the reaction zone and below the phase separator.

40. A method of separating a liquid and a gas within an upflow reactor apparatus having a reaction zone, comprising
(a) providing an upflow of the liquid and the gas within the upflow reactor apparatus such that the liquid and gas flow upwardly from the reaction zone into a first phase separator having a first wall having a first side and a second side and a second wall having a first side and a second side, the second side of the first wall and the first side of the second wall defining a coagulation area, the first wall adjoining a deflector inclined to the horizontal and vertical, and a plurality of parallel plates spaced from each other and vertically and horizontally inclined, each of the parallel plates having a lower edge, the second wall adjoining one of the parallel plates and the deflector extending below and across the lower edges of the parallel plates;
(b) providing a liquid circulation around the parallel plates by diverting gas away from the coagulation area to a gas collecting area, wherein the liquid circulation provides a downwardly directed flow around the parallel plates of the first phase separator and liquid is directed toward the coagulation area;

(c) directing the diverted gas from the gas collecting area out of the upflow reactor apparatus through a gas outlet;

(d) directing liquid from the coagulation area into a second separator which may be the same or different from the first phase separator and which is located above the first phase separator; and (e) removing liquid from the upflow reactor apparatus through an outlet above the at least one second separator.

41. The method according to claim 40, wherein step (d) further comprises passing the liquid through a clarification zone between the first phase separator and the second separator before directing the liquid into the second separator.

42. The method according to claim 40, wherein the reaction zone is an anaerobic fermentation reaction zone.

43. The method according to claim 40, further comprising separating a solid from the liquid and the gas by directing the solid downwardly along the deflector to the reaction zone.

44. The method according to claim 43, wherein the reaction zone is an anaerobic fermentation reaction zone and the liquid is waste water, the solid is biomass and the gas is generated within the reaction zone.

45. The method according to claim 40, further comprising removing clarified liquid from a clarification zone in liquid communication with the at least one second separator and above the at least one second separator.

46. The method according to claim 40, wherein the second separator is the same as the first phase separator.

* * * * *